United States Patent
DeMan et al.

(10) Patent No.: US 9,237,874 B2
(45) Date of Patent: Jan. 19, 2016

(54) METHOD AND SYSTEM FOR NON-INVASIVE IMAGING OF A TARGET REGION

(75) Inventors: Bruno Kristiaan Bernard DeMan, Clifton Park, NY (US); James Vradenburg Miller, Clifton Park, NY (US); Floribertus P. M. Heukensfeldt Jansen, Ballston Lake, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 13/459,585

(22) Filed: Apr. 30, 2012

(65) Prior Publication Data

US 2013/0284939 A1    Oct. 31, 2013

(51) Int. Cl.
| | |
|---|---|
| G01T 1/161 | (2006.01) |
| A61B 6/03 | (2006.01) |
| G06T 11/00 | (2006.01) |
| A61B 6/12 | (2006.01) |
| A61B 6/00 | (2006.01) |
| A61B 6/06 | (2006.01) |

(52) U.S. Cl.
CPC . *A61B 6/032* (2013.01); *A61B 6/12* (2013.01); *A61B 6/4021* (2013.01); *A61B 6/4241* (2013.01); *A61B 6/469* (2013.01); *A61B 6/482* (2013.01); *A61B 6/488* (2013.01); *G06T 11/005* (2013.01); *A61B 6/037* (2013.01); *A61B 6/06* (2013.01); *A61B 6/4417* (2013.01)

(58) Field of Classification Search
CPC ....... G06T 11/005; A61B 6/032; A61B 6/488
USPC ............. 250/363.1, 363.01, 363.02; 378/4, 8, 378/20; 382/131
See application file for complete search history.

(56) References Cited

U.S. PATENT DOCUMENTS 5,355,309 A * 10/1994 Eberhard et al. ................ 378/15
7,116,749 B2  10/2006 Besson
(Continued)

FOREIGN PATENT DOCUMENTS

WO    2010070554 A1    6/2010

OTHER PUBLICATIONS

Lee et al.; "Small Animal X-ray Micro-CT with Zoom-in Imaging Capability", IEEE Nuclear Science Symposium Conference Record, 2006, vol. 5, pp. 3102-3105, Oct. 29-Nov. 1, 2006.

(Continued)

Primary Examiner — David Porta
Assistant Examiner — Jeremy S Valentiner
(74) Attorney, Agent, or Firm — Scott J. Asmus (57) ABSTRACT

Embodiments of systems, methods and non-transitory computer readable media for imaging are presented. Preliminary image data corresponding to a first FOV of a subject at a first resolution is acquired using an imaging system including one or more radiation sources and at least one hybrid detector, specifically using at least one section of the hybrid detector having the first resolution. The target ROI is identified using the preliminary image data. Further, the subject is positioned to align the target ROI along a designated axis. Additionally, parameters associated with the sources, the hybrid detector and/or an imaging system gantry are configured for acquiring target image data at a second resolution greater than the first resolution using at least one section of the hybrid detector having the second resolution. Further, one or more images corresponding to at least the target ROI are reconstructed using the target and/or the preliminary image data.

18 Claims, 9 Drawing Sheets

(56) References Cited

U.S. PATENT DOCUMENTS

| | | | |
|---|---|---|---|
| 7,227,923 B2 | 6/2007 | Edic et al. | |
| 7,333,587 B2 | 2/2008 | De Man et al. | |
| 7,372,934 B2 | 5/2008 | De Man et al. | |
| 7,697,658 B2 | 4/2010 | Wang et al. | |
| 7,840,249 B2 | 11/2010 | Wang et al. | |
| 8,045,771 B2 | 10/2011 | Tao et al. | |
| 2002/0176530 A1* | 11/2002 | Okumura et al. | 378/19 |
| 2004/0062342 A1* | 4/2004 | Cahill | 378/4 |
| 2005/0119565 A1* | 6/2005 | Pescatore | 600/429 |
| 2007/0242806 A1* | 10/2007 | Borgmann et al. | 378/207 |
| 2008/0075225 A1* | 3/2008 | Kalender | 378/20 |
| 2008/0187095 A1 | 8/2008 | Boone et al. | |
| 2009/0225934 A1* | 9/2009 | Hugg et al. | 378/20 |
| 2009/0245467 A1* | 10/2009 | Wilson et al. | 378/111 |
| 2010/0266181 A1* | 10/2010 | Oeckl et al. | 382/131 |
| 2010/0277312 A1* | 11/2010 | Edic et al. | 340/540 |
| 2011/0051886 A1* | 3/2011 | Basu et al. | 378/8 |
| 2011/0051895 A1 | 3/2011 | Vogtmeier et al. | |
| 2012/0063659 A1* | 3/2012 | Wang et al. | 382/131 |

OTHER PUBLICATIONS

Li-Nan et al.; "Applied Research on the Automatic Detection of Lung Nodules ROI Based on Top-Hat and Gabor Filter", Third International Symposium on Information Processing (ISIP 2010), pp. 533-536, Oct. 15-17, 2010.

Michael Knaup et al.; 'Simple ROI Cone-Beam Computed Tomography; IEEE NSS/MIC Conference Record, 2010; pp. 194-199.

D.J. Gentle et al.; "Region of interest tomography in industrial applications": Department of Physics, University of Surrey, Guildford GU2 5XH, UK; Available online Oct. 28, 2002; Abstract 1 Page.

Lingyun Chen et al.; "Dual resolution cone beam breast CT: A feasibility study"; Med Phys. Sep. 2009; 36 (9): 4007-4014. Published online Aug. 12, 2009. doi: 10.1118/1.3187225, pp. 1-11.

Lingyun Chen et al; "Feasibility of volume-of-interest (VOI) scanning technique in cone beam breast CT—a preliminary study"; Med Phys. Aug. 2008; 35(8): 3482-3490. Published online Jul. 8, 2008. doi: 10.1118/1.2948397, pp. 1-13.

V. Patel et al.; "Rotational micro-CT using a clinical C-arm angiography gantry"; Med Phys. Oct. 2008; 35(10): 4757-4764. Published online Sep. 26, 2008. doi: 10.1118/1.2989989, pp. 1-9.

Rohkohl et al, "Technical Note: RabbitCT—an open platform for benchmarking 3D cone-beam reconstruction algorithms", Medical Physics 36, 3940 (2009); doi: 10.1118/1.3180956, American Association of Physicists in Medicine, pp. 3940-3944, Aug. 12, 2009.

* cited by examiner

METHOD AND SYSTEM FOR NON-INVASIVE IMAGING OF A TARGET REGION

BACKGROUND

Non-invasive imaging techniques are widely used in security screening, quality control, and medical diagnostic systems. Particularly, in medical imaging, non-invasive imaging techniques such as multi-energy imaging allow for unobtrusive, convenient and fast imaging of underlying tissues and organs. To that end, radiographic imaging systems such as nuclear medicine (NM) gamma cameras, computed tomography (CT) systems and positron emission tomography (PET) systems employ a plurality of radiation sources and detectors.

CT systems, for example, typically include an X-ray source and a detector array that may be configured to acquire projection data from different angular positions around the object using a rotatable gantry or by rotating the object. Particularly, the detector array in a CT system employs one or more elements for converting X-ray photon energy into current signals that are integrated over a time period, measured, and ultimately digitized. Certain CT systems include photon counting (PC) detectors that provide dose efficient X-ray spectral information, energy discrimination (ED) and material decomposition capabilities. Certain other CT systems employ energy integrating (EI) detectors capable of operating at high X-ray flux rates. In certain implementations, however, the CT systems employ both PC and EI detectors such that the imaging system may combine energy information provided by ED detector cells with high flux capability and high signal-to-noise ratio (SNR) provided by the EI detector cells for use in reconstructing images.

Although the conventional detector cells provide varied functionality, a particularly challenging task is to configure detector settings for imaging a targeted ROI that is less than the full scan field of view (FOV) of the imaging system in high spatial resolution. By way of example, certain imaging modalities may need to generate high-resolution images of certain regions of the lungs, coronary vessels and/or tissues. As the lung field is adjacent to the coronary vessels and the sternum, high flux and low flux regions are proximally positioned and are encountered at the detector in rapid succession in time. Accordingly, application of conventional reconstruction methods may result in image blurring and other artifacts that can severely affect clinical diagnosis, especially if the imaged features are small. For example, plaques formed in coronary arteries are generally indicative of a risk of a potential heart attack, but are difficult to image due to their small size.

Certain conventional imaging systems, for example, have employed expensive detector configurations, heavier or higher power tubes combined with fast spinning of a gantry, and complex iterative reconstructions to generate high-resolution images. These techniques, however, incur considerable costs, are mechanically restrictive and/or rely on additional imaging time and radiation dosage, especially for reconstructing small features such as lesions and nodules in regions of interest.

BRIEF DESCRIPTION

Certain aspects of the present technique are drawn to methods, systems and non-transitory computer readable media for imaging a subject. Preliminary image data corresponding to a first field of view of the subject at a first resolution is acquired using an imaging system. To that end, the imaging system includes one or more radiation sources and at least one hybrid detector responsive to radiation received from the one or more radiation sources. Particularly, the preliminary image data is acquired using at least one section of the hybrid detector having the first resolution. A target region of interest is identified based on the preliminary image data. Further, the subject is positioned so as to align the target region of interest along a designated axis. Additionally, one or more parameters associated with the radiation sources, the hybrid detector and/or a gantry associated with the imaging system are configured for acquiring target image data corresponding to the target region of interest at a second resolution greater than the first resolution. Specifically, the target image data is acquired using at least one section of the hybrid detector having the second resolution. Further, one or more images corresponding to at least the target region of interest are reconstructed using the target image data and/or the preliminary image data.

DRAWINGS

These and other features and aspects of embodiments of the present technique will become better understood when the following detailed description is read with reference to the accompanying drawings in which like characters represent like parts throughout the drawings, wherein.

DETAILED DESCRIPTION

The following description presents exemplary systems and methods for acquiring sufficient data for reconstruction of a high-resolution image of a targeted region of interest (ROI) of a subject. Particularly, embodiments illustrated hereinafter disclose imaging systems and methods for acquiring image data for enhanced image reconstruction of a targeted ROI. Although exemplary embodiments of the present technique are described in the context of a CT system, it will be appreciated that use of the present technique in various other imaging applications and systems is also contemplated. Some of these systems may include a positron emission tomography (PET)-CT scanner, a single or multiple source imaging system, a single or multiple detector imaging system, a single photon emission computed tomography (SPECT)-CT scanner and/or X-ray tomosynthesis systems.

Further, in addition to medical imaging, the techniques and configurations discussed herein are applicable in other non-invasive imaging contexts, such as baggage or package screening or industrial nondestructive evaluation of manufactured parts. An exemplary environment that is suitable for practicing various implementations of the present technique is discussed in the following sections with reference to FIGS. 1 and 2.

Figure 1:
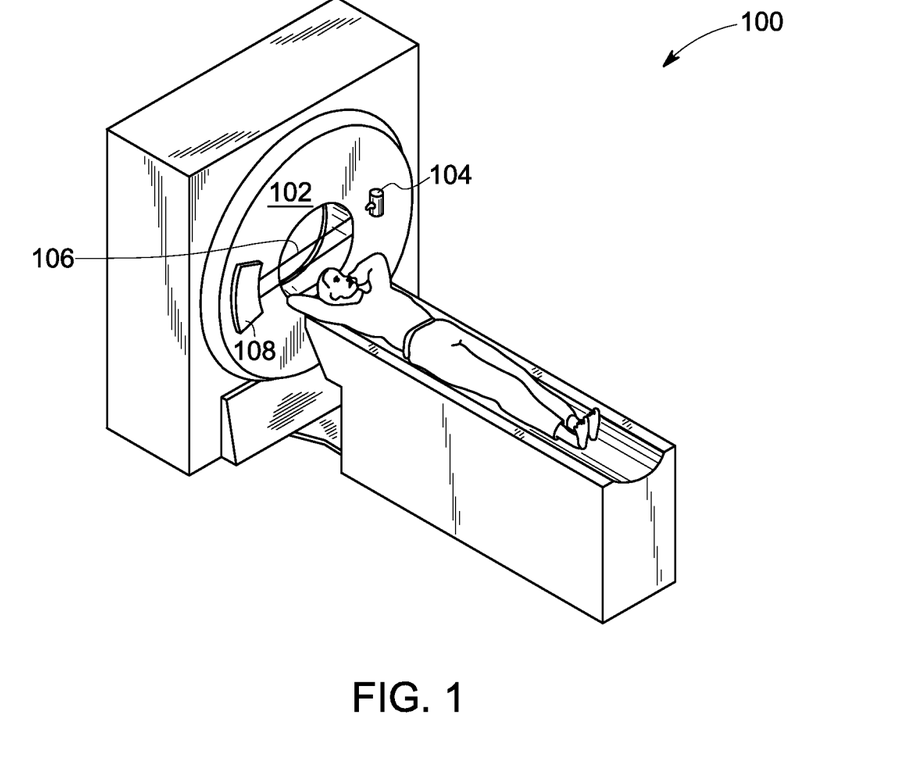
FIG. 1 is a pictorial view of an exemplary imaging system for scanning a target region of interest in high spatial resolution, in accordance with aspects of the present technique.

FIG. 1 illustrates an exemplary imaging system 100 for acquiring and processing image data. In one embodiment, the imaging system 100 corresponds to a CT system including a gantry 102, and designed to acquire image data, for example, at two or more X-ray energy levels for further display and/or analysis. In certain embodiments, however, the system 100 is configured to acquire image data using a single X-ray source spectrum.

Accordingly, in one embodiment, the system 100 includes at least one radiation source 104 such as an X-ray tube that projects a beam of X-ray radiation 106 towards a detector array 108, for example, positioned on the opposite side of the gantry 102. The X-ray beams 106 typically include a fan beam, a cone beam, or a parallel beam. In certain embodiments, multiple radiation sources may be employed to project a plurality of X-ray beams 106 for acquiring image data from different view angles. In certain other embodiments, the radiation source 104 is a distributed source configured to emit X-ray beams 106 from multiple locations along a surface. To that end, the distributed radiation source 104, for example, includes one or more addressable solid-state emitters configured as one or multi-dimensional field emitter arrays.

In one embodiment, the system 100 acquires image data for reconstructing one or more high-resolution images of a target ROI by adapting one or more imaging parameters corresponding to the gantry 102, the radiation source 104 and/or the detector array 108. The target ROI, for example, includes a region that is typically smaller than the full scan field of view (FOV) of the system 100. While imaging the thorax, for example, a high-resolution image of a target ROI of a patient's lungs may be desired for diagnosing lung cancer. Particularly, the system 100 configures the scan sequence and/or various imaging parameters for acquiring sufficient image data corresponding to the target ROI even when using low doses of radiation. Certain exemplary configurations of the system 100 that facilitate image data acquisition for reconstructing high quality image of the target ROI in accordance with aspects of the present technique will be described in greater detail with reference to FIG. 2.

Figure 2:
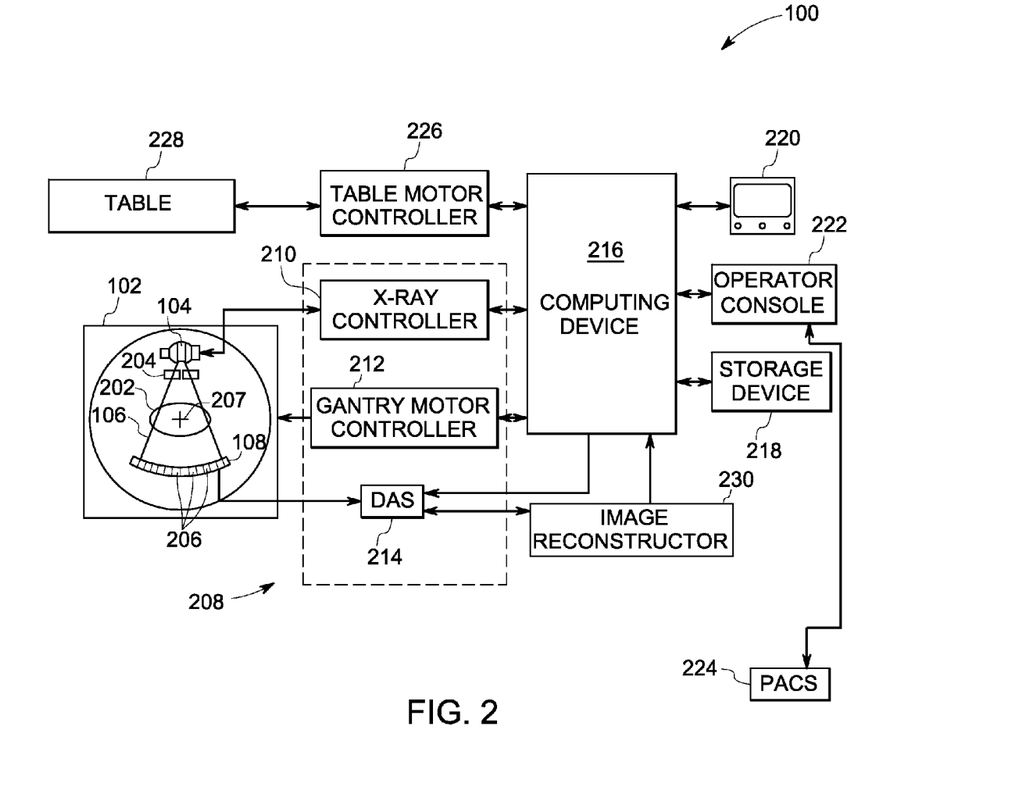
FIG. 2 is a schematic diagram illustrating exemplary components of the imaging system illustrated in FIG. 1, in accordance with aspects of the present technique.

FIG. 2 is a diagrammatic illustration of exemplary components of the imaging system 100 of FIG. 1. In one embodiment, the system 100 performs a preliminary scan of a desired FOV of a subject 202, such as a medical patient or a baggage. To that end, the radiation source 104 projects, for example, fan-shaped or cone-shaped X-ray beams 106 for imaging the desired FOV of the subject 202. Particularly, the system 100 configures one or more parameters of the radiation source 104 to focus the X-ray beams 106 on the target ROI based on a designated configuration of the detector array 108 and/or a desired method of data acquisition.

Accordingly, in one embodiment, the system 100 includes a collimator 204 positioned proximate the radiation source 104 to define the size and shape of the one or more X-ray beams 106 that pass through the desired FOV of the subject 202. The collimator 204 collimates the X-ray beams 106 based on specific imaging or application requirements using one or more collimating regions, for example, defined using lead or tungsten shutters. The X-ray beams 106 pass through the subject 202 and are attenuated by the subject's anatomy. The attenuated portion of the X-ray beams 106 impacts one or more regions of the detector array 108.

In one embodiment, the detector array 108 includes a plurality of detector elements 206 that together sense the projected X-ray beams 106 that pass through the subject 202. In certain embodiments, the detector array 108 is fabricated in a multi-slice configuration that includes a plurality of rows of cells or detector elements 206. In such a configuration, the detector array 108 includes one or more additional rows of the detector elements 206 arranged in a parallel configuration for acquiring projection data. In one embodiment, the detector elements 206 produce an electrical signal representative of the intensity of the impinging X-ray beams 106, which in turn, can be used to estimate the attenuation of the X-ray beams 106 as they pass through the subject 202. In another embodiment, the detector elements 206 determine a count of incident photons in the X-ray beams 106 and/or determine corresponding energy.

Alternatively, in certain embodiments, the detector array 108 corresponds to a hybrid detector that includes a combination of one or more energy integrating (EI) detector elements 206 and one or more energy discriminating (ED) detector elements 206 arranged in one or more desired configurations. The EI detector elements 206 in the hybrid detector array 108 produce an electronic signal proportional to the total amount of absorbed X-ray energy in each view. Further, the ED detectors may provide information regarding the energy distribution of the detected photons by producing two or more signals corresponding to two or more energy intervals, for example, a high-energy signal and a low-energy signal.

In one embodiment, the plurality of detector elements 206 in the hybrid detector array 108 differs in size and/or energy sensitivity. Additionally, in an exemplary configuration of the system 100, one or more of the detector elements 206 of the hybrid detector array 108 can be selectively configured for scanning a desired FOV of the subject 202 at a desired resolution. To that end, in one embodiment, the detector elements 206 acquire electrical signals corresponding to the generated X-ray beams 106 at a variety of angular positions around the subject 202 for collecting a plurality of radiographic projection views for image construction. Particularly, during a scan to acquire the projection data, the gantry 102 and the components mounted thereon may rotate about a center of rotation 207. However, in certain embodiments where a projection angle relative to the imaged subject 202 varies as a function of time, the mounted components may move along a general curve rather than along a segment of a circle.

Thus, in one embodiment, the system 100 includes a control mechanism 208 that controls the rotation of the gantry 102 and the operation of the radiation source 104 to acquire projection data from a desired view angle of the radiation source 104. The control mechanism 208, for example, includes an X-ray controller 210 that provides power and timing signals to the radiation source 104 and a gantry motor controller 212 that controls the rotational speed and position of the gantry 102 based on scanning requirements. The control mechanism 208, in one embodiment, further includes a data acquisition system (DAS) 214 for sampling analog data from the detector elements 206 and converting the analog data to digital signals for subsequent processing.

The data sampled and digitized by the DAS 214 is input, for example, to a computing device 216. The computing device 216 stores this data in a storage device 218, such as a hard disk drive, a floppy disk drive, a compact disk-read/write (CD-R/W) drive, a Digital Versatile Disc (DVD) drive, a flash drive, or a solid state storage device. In certain embodiments, the computing device 216 includes modules and/or applications that allow for automated analysis of the acquired image data for estimating location of a target ROI for further evaluation. The target ROI corresponds to at least a portion of the desired FOV of the subject 202 that was evaluated during the preliminary scan.

Typically, the preliminary scan data, for example, includes imaging system and tissue parameters. The system parameters, for example, include one or more operating parameters associated with the radiation source 104 and/or the detector elements 206. Additionally, the tissue parameters, for example, include structure, thickness, eccentricity, density and/or mass of the desired FOV of the subject 202. Typically, at least a portion of biological tissues such as cardiac tissues, liver tissues, breast tissues, prostate tissues, thyroid tissues, lymph nodes or vascular structures may exhibit different composition, density, shape, size and/or structure in comparison to normal tissue indicating an onset or presence of a disease or medical condition such as cancer, tumor, fibrosis or steatosis.

Accordingly, in one embodiment, the computing device 216 analyzes the tissue parameters using automated analysis tools as these parameters are closely linked to tissue state with respect to pathology. In certain embodiments, the computing device 216 uses operator input in addition to the preliminary scan data for identifying the target ROI. To that end, in one embodiment, the computing device 216 is coupled to a display 220 that allows an operator to observe scanned images and other relevant information to indicate the target ROI, for example, using a graphical user interface (GUI). The operator can also specify commands and scanning parameters via an operator console 222, which may include a keyboard (not shown).

Although FIG. 2 illustrates only one operator console 222, more than one operator workstation may be coupled to the system 100, for example, for inputting or outputting system parameters, requesting examinations and/or viewing images. Further, in certain embodiments, the system 100 is coupled to multiple displays, printers, workstations, and/or similar devices located either locally or remotely, for example, within an institution or hospital, or in an entirely different location via one or more configurable wired and/or wireless networks such as the Internet and virtual private networks.

In one embodiment, for example, the operator console 222 either includes, or is coupled to a picture archiving and communications system (PACS) 224. In an exemplary implementation, the PACS 224 is further coupled to a remote system such as a radiology department information system, hospital information system and/or to an internal or external network (not shown) to allow operators at different locations to supply commands and parameters and/or gain access to the image data.

The computing device 216 uses the operator supplied and/or system defined commands and parameters to operate a table motor controller 226 that, in turn, controls a motorized table 228. Particularly, the table motor controller 226 moves the table 228 for appropriately positioning the subject 202 in the gantry 102 to enable the detector elements 206 to acquire projection data corresponding to the target ROI of the subject 202. In one example, upon identifying the target ROI, the computing device 216 directs the table motor controller 226 to move the table 228 so as to center the target ROI of the subject 202 longitudinally or trans-axially at the iso-center of the imaging system 100. Alternatively, the computing device 216 provides appropriate commands and parameters to one or more of the DAS 214, the X-ray controller 210 and the gantry motor controller 212 to configure the system 100 for imaging the target ROI.

Particularly, the computing device 216 reconfigures one or more parameters of the detector array 108 and/or the radiation source 104 to scan the target ROI at a higher resolution than the preliminary scan. The computing device 216 performs the reconfiguration, for example, by employing a smaller focal spot size to focus on the target ROI by changing the focusing parameters of the radiation source 104, using a different focal spot in the radiation source 104 or operating another X-ray source having an appropriate focal spot size. In certain embodiments, the computing device 216 uses the detector elements 206 having higher resolution to focus on the target ROI. To that end, the computing device 216 allows for selectively activating a portion of the detector array 108 having smaller detector elements 206. In yet another configuration, the readout electronics of the detector array is reconfigured so as to create smaller detector elements.

In certain other embodiments, the computing device 216 reconfigures the system 100 to operate in a multi-energy mode. To that end, the computing device 216 allows for switching the tube voltage of the radiation source 104 or using a high-resolution portion of the detector array 108 for acquiring data corresponding to the target ROI. Accordingly, in certain embodiments, the computing device 216 includes additional circuitry, such as a switching interface, for switching the radiation source 104 and one or more of the detector elements 206 between the selected operating modes. Alternatively, the computing device 216 transmits digital signals to the X-ray controller 210 and DAS 214 for switching the radiation source 104 and one or more of the detector elements 206 between the selected operating modes based on the reconfigured parameters. The system 100, using the reconfigured parameters, then performs a high-resolution scan of the target ROI.

In conventional imaging modalities, such as certain micro-CT systems, low and high-resolution imaging is performed using two or more distinct imaging modalities having low and high-resolution, respectively. Such conventional devices, thus, entail additional costs and radiation dosage administered to the subject 102. The hybrid detector array 108, however, allows the system 100 to perform both the high and low-resolution scans using the same imaging system 100. Additionally, limiting the high-resolution targeted scan to only the target ROI using the hybrid detector array 108 substantially reduces the radiation dose administered to the subject 202, while allowing acquisition of image data for reconstructing one or more high-resolution images of the target ROI without increasing image noise.

Further, in certain embodiments, the computing device 216 communicates the targeted scan data to an image reconstructor 230. In one embodiment, the image reconstructor 230 reconstructs a high quality image of the target ROI, for example, using interior tomography. In certain embodiments, the image reconstructor 230 uses certain a priori information provided by the computing device 216 for reconstructing an image of the target ROI. The a priori information, in one example, includes a correlation between an operational setting of the detector elements 206 and/or the radiation source 104 and a particular view angle. In another example, the a priori information includes preliminary scan data and any information relating to the scanned subject 202 acquired before the CT scan or input by the user through the operator console 222. In certain other examples, the a priori information may also include a previously determined model of the target organ and/or the imaging geometry of the system 100.

In one embodiment, the preliminary scan data finds use in establishing the subject size, shape and density profile. In certain embodiments, the image reconstructor 230 employs the preliminary scan data and/or the a priori information along with the targeted scan data for reconstructing an image corresponding to the target ROI. Alternatively, the image reconstructor 230 uses sinogram data generated using the preliminary scan to complement the sinogram data generated from the targeted scan of the target ROI for image reconstruction. Use of the additional sinogram data allows for reconstructing images including one or more features of the target ROI in high spatial resolution.

In one embodiment, the image reconstructor 230 transmits the reconstructed images to the display 220 to allow the operator to observe and assess, for example, a state of the imaged tissues of the subject 202 with respect to pathology. Alternatively, the image reconstructor 230 transmits the reconstructed images to the computing device 216 for further evaluation. In one embodiment, the computing device 216 employs one or more analytical tools and/or algorithms to assess a pathological condition of the imaged issues. Use of the high-resolution images of the target ROI allows for detection of any unusual features in the target ROI, which in turn allows for an accurate assessment of the medical condition of the subject 202.

Further, performing a second high-resolution scan only for the target ROI by reconfiguring one or more parameters of the system 100 allows for reduction in the radiation dose administered to the patient. Additionally, the targeted scan allows for relatively artifact-free images, while providing features of interest in high spatial resolution for accurate and early diagnosis of conditions such as cardiac vulnerable plaque and many lung diseases. Certain exemplary methods for acquiring and processing image data for reconstructing the high quality image of a smaller ROI in a larger FOV will be described in greater detail with reference to FIGS. 3-8.

Figure 3:
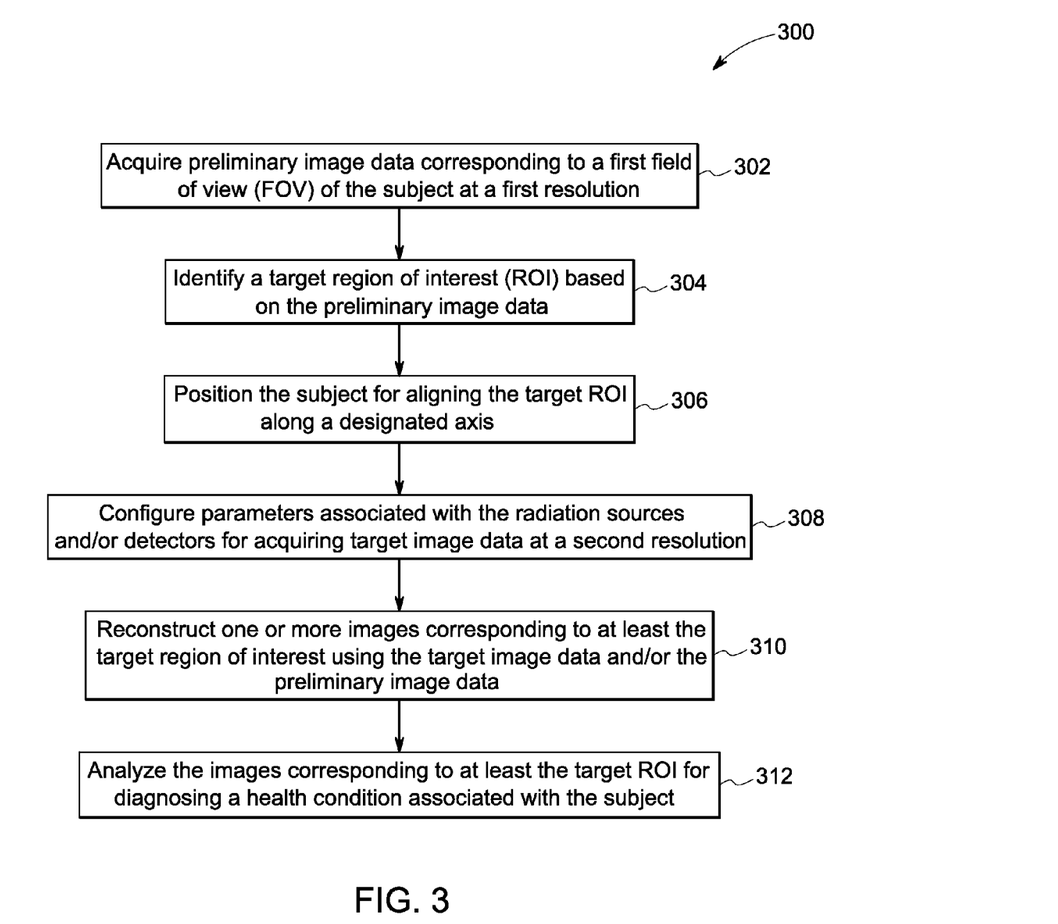
FIG. 3 is a flowchart depicting an exemplary method for imaging a target region of interest in high spatial resolution using a hybrid detector, in accordance with aspects of the present technique.

FIG. 3 illustrates a flow chart 300 depicting an exemplary method for imaging a target ROI of a subject in high-resolution using a hybrid detector. The exemplary method may be described in a general context of computer executable instructions on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 3, the exemplary method is illustrated as a collection of blocks in a logical flow chart, which represents operations that may be implemented in hardware, software, or combinations thereof. The various operations are depicted in the blocks to illustrate the functions that are performed, for example, during imaging system configuration, image data acquisition and processing, and image reconstruction phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Generally, non-invasive imaging techniques such as tomographic imaging are used to generate two or three-dimensional images for various diagnostic and/or prognostic purposes. Conventional imaging techniques allow for a tradeoff between various imaging criteria such as image quality, spatial resolution, noise, radiation dose, system size and associated costs. Certain clinical applications, however, entail use of images in high spatial resolution for investigating minute features within a subject, such as in and around a human heart. Particularly, accurate characterization of specific features, for example, corresponding to the thoracic cavity allows for a better understanding of the physiology of heart and lungs, which in turn, aids in early detection of various cardiovascular and lung diseases.

Accordingly, embodiments of the present method describe a technique for generating high quality diagnostic images using a cost effective imaging system, while reducing the radiation dosage typically administered to a patient. To that end, at step 302, an imaging system, such as the imaging system 100 of FIGS. 1-2, acquires preliminary image data corresponding to a first FOV of a subject, such as a person or a baggage, at a first resolution. As previously noted, the preliminary image data includes, for example, parameters of the subject such as structure, thickness, eccentricity, density and mass. Further, the preliminary image data also includes, for example, system parameters such as one or more operational settings corresponding to the detector elements 206 and the radiation source 104.

The system 100 acquires the preliminary image data using a preliminary scan or a scout scan at a first resolution. To that end, in certain embodiments, an operator supplies system parameters such as type of imaging required, mA and kVp values and desired spatial resolution to the system 100 to setup the preliminary scan of the first FOV of the subject at the first resolution. In one example, the first FOV includes a patient's torso including the region of the heart. In other examples, however, the first FOV corresponds to a smaller area, such as the lung or heart of a human subject imaged in the first resolution. Furthermore, in certain embodiments, the first resolution corresponds to a low-fidelity and/or a single energy preliminary scan to obtain preliminary image data, for example, corresponding to anatomical structure, thickness, eccentricity, density and mass of the first FOV of the subject 202.

At step 304, the system 100 employs the acquired preliminary image data to identify a target ROI of the subject 202. In one embodiment, the system 100 displays the preliminary image data and/or one or more corresponding images on the display 220 for evaluation by an operator. The operator analyzes the preliminary image data and/or corresponding images to identify the target ROI from the acquired preliminary image data corresponding to the first FOV. Specifically, in one example, the operator reviews the preliminary image data indicative of regions of increased thickness as compared to surrounding tissues in the first FOV to identify the target ROI using a GUI.

Alternatively, the system 100 employs computer aided evaluation, automated tools and/or applications for identifying the target ROI. The automated tools, for example, use one or more techniques such as segmentation or identifying specific signatures of the structures using matched filters or Eigen analysis for identifying the target ROI. In certain embodiments, the target ROI is identified based on any structural anomalies such as lesions or nodules detected during previous examinations.

The system 100, at step 306, positions the subject to align the target ROI along a designated axis for imaging. Particularly, in one embodiment, the subject 202 is positioned such that the target ROI is at iso-center and centered longitudinally in the system 100. Alternatively, the subject 202 is positioned to align the target ROI, for example, along a designated transaxial plane. In one implementation, the computing device 216 employs the table motor controller 226 for positioning the subject 202. Specifically, the table motor controller 226 moves the table 228 for appropriately positioning the subject 202 in the gantry 102 along the designated axis to enable the detector elements 206 to acquire projection data corresponding to the target ROI. In another embodiment, the computing device 216 provides appropriate commands and parameters to one or more components of the control mechanism 208 to configure the radiation source 104 and the detector elements 206 for imaging the target ROI.

In an alternative embodiment, instead of positioning the patient to align the target ROI, the computing device 216 tracks the target ROI. To that end, the computing device 216 focuses the X-ray beams 106 on the target ROI. Additionally, the computing device 216 configures readout circuitry (not shown) for a narrow or a desired portion of the detector array 108, while selectively changing the spatial resolution of the specific detector elements 206 for use in imaging the target ROI. To that end two or more adjacent detector elements 206 may be summed into a single bin for low resolution imaging, or may be binned into individual bins for high resolution imaging, by switching between low and high resolution settings for the detector array 108. Tracking the ROI using reconfigured parameters in place of re-centering the patient mitigates the need for a large table, minimizes mechanical motion and centering-related issues during imaging.

Further, at step 308, the computing device 216 configures one or more parameters associated with the one or more radiation sources 104 and/or detector elements 206 for acquiring target image data corresponding to the target ROI at a second resolution. In a presently contemplated embodiment, the second resolution is substantially higher than the first resolution used to scan the first FOV. In certain embodiments, the computing device 216 determines the first resolution by summing signals received from the plurality of detector elements 206 and the second resolution by having each of the detector elements 206 read out individually.

Further, in one example, configuring the one or more parameters include employing the collimator 204 to define the size and shape of the X-ray beams 106 to focus specifically on the target ROI. In another example, the system 100 employs a small focal spot size for imaging the target ROI. Accordingly, in one embodiment, the system 100 configures the focusing parameters of the radiation source 104 for achieving the small focal spot size. Alternatively, the system 100 employs a different focal spot in the X-ray radiation source 104 or another X-ray tube having appropriate imaging parameters for imaging the target ROI in the second resolution.

In certain embodiments, configuring the one or more parameters may also include using the detector elements 206 having the second or higher resolution to focus on the target ROI. To that end, the computing device 216 allows for selectively activating a portion of the hybrid detector array 108 having smaller detector elements 206. Further, in one embodiment, the computing device 216 reconfigures the system 100 to operate in a multi-energy mode by switching the tube voltage of the radiation source 104 using a high-resolution portion of the hybrid detector array 108 for acquiring data corresponding to the target ROI.

Accordingly, in certain implementations, the computing device 216 includes additional circuitry, such as a switching interface, for selectively operating or switching the radiation source 104 and one or more of the detector elements 206 between the selected operating modes. Alternatively, the computing device 216 transmits digital signals to the X-ray controller 210 and/or the DAS 214 for switching the radiation source 104 and one or more of the detector elements 206 between the selected operating modes or selectively operating the various X-ray sources and detectors coupled to the system 100 based on the reconfigured parameters. In one embodiment, the computing device 216 and/or the control mechanism 208 may also be configured to adjust the relative tube currents of the radiation source 104 and/or the relative operational settings of the hybrid detector array 108.

The system 100 uses the reconfigured parameters to perform a high-resolution targeted scan of the target ROI, for example using multiple energy protocols or fast mA and kVp switching. The system 100 then communicates the targeted scan data to the image reconstructor 230. At step 310, the image reconstructor 230 uses the targeted scan data to reconstruct one or more high-resolution images of the target ROI. To that end, in one embodiment, the image reconstructor 230 employs interior tomography for reconstructing images using truncated data. In particular, the image reconstructor 230 may use the truncated limited-angle projection data that allows exact interior reconstruction of the target ROI based on the linear attenuation coefficient distribution of a sub-region within the target ROI.

In certain embodiments, the image reconstructor 230 uses a priori information provided by the computing device 216 in addition to the targeted scan data for reconstructing an image of the target ROI. As previously noted, the a priori information, in one example, may include the preliminary scan data that may be used to tune operational settings for the targeted scan. Alternatively, the a priori information includes a previously determined model of a target organ, system geometry, preliminary scan data and/or any information relating to the scanned subject 202 acquired before the CT scan or input by the user through the operator console 222.

At step 312, the computing device 216 analyzes the reconstructed images corresponding to at least the target ROI for diagnosing a health condition associated with the subject. To that end, in one embodiment, the image reconstructor 230 transmits the reconstructed images to the display 220 to allow the operator to observe and assess, for example, a pathological state of the imaged tissues of the subject 202. Alternatively, the image reconstructor 230 transmits the reconstructed images to the computing device 216 for further analysis. In certain embodiments, the computing device 216 employs one or more analytical tools and/or algorithms, for example, to identify nodules, stenosis and plaques and assess corresponding size, growth, density, composition and malignancy. Use of the high-resolution images of the target ROI allows for detection of any unusual features in the target ROI, and thus, in a more informed assessment of the medical condition of the subject 202.

Use of the hybrid detector array 108 for performing the high-resolution scan only for the target ROI reduces the radiation dose typically administered to the patient without use of additional imaging equipment. Further, reconfiguring one or more parameters of the system components for changing the position and resolution for different scans enables use of an efficient imaging system that may be adapted for reconstructing features of interest in high spatial resolution for accurate and early diagnosis of medical conditions.

Figure 4:
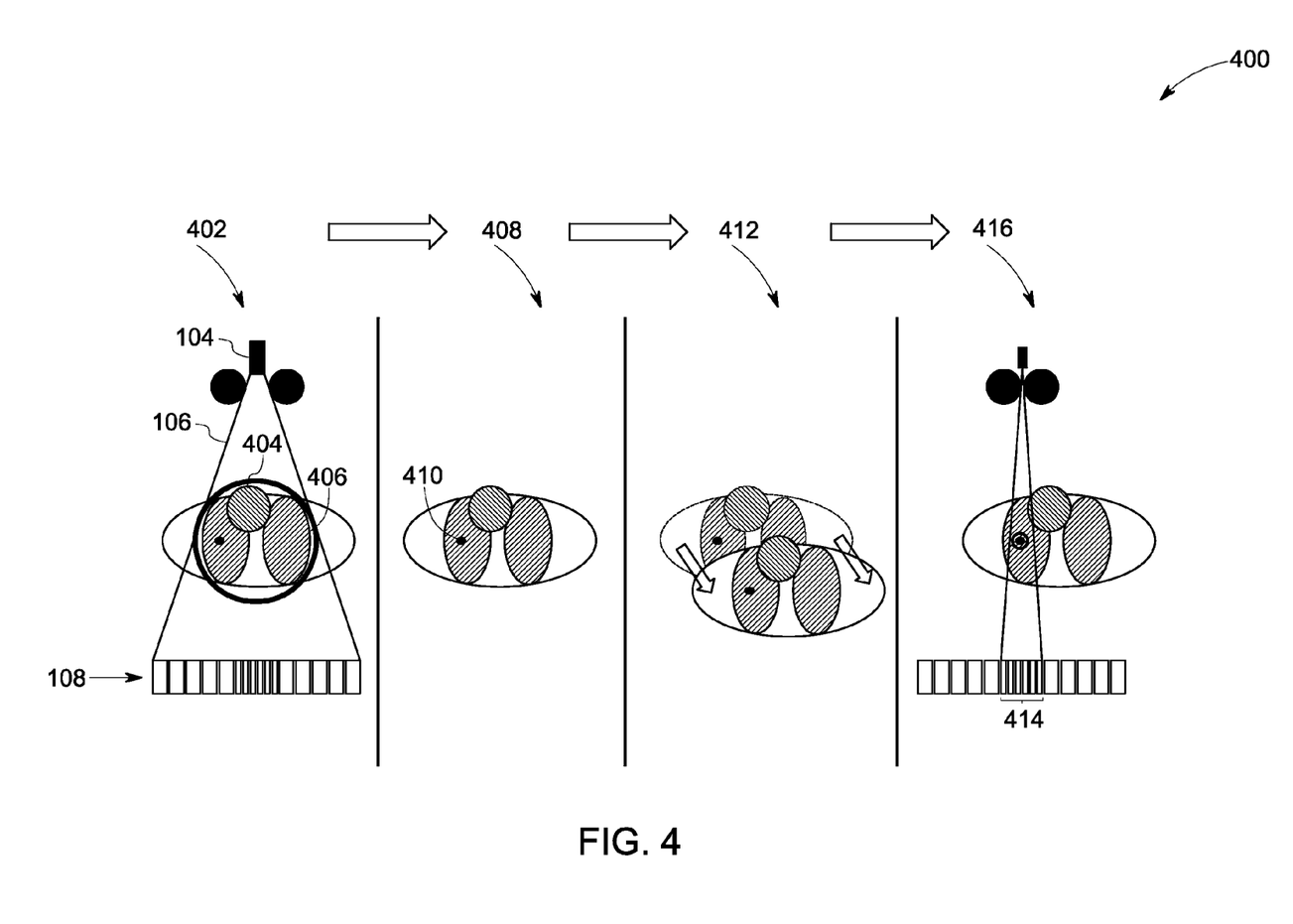
FIG. 4 is a flowchart depicting an exemplary sequence of operations for imaging lung tissues of a subject using the method described with reference to FIG. 3, in accordance with aspects of the present technique.

Certain exemplary configurations of the radiation source and the detector elements for tomographic imaging of the first FOV using a low-resolution preliminary scan and the target ROI using a high-resolution targeted scan are illustrated in FIGS. 4-9. Particularly, FIG. 4 depicts an exemplary sequence 400 of operations for imaging the lung and cardiac tissues using the method described with reference to FIG. 3. As illustrated in FIG. 4, at step 402, the radiation source 104 focuses on the first FOV, that is, the thoracic cavity including the heart 404 and lungs 406 of the subject 202. In an exemplary implementation, the imaging system 100 performs a single energy CT scan of the first FOV at a first resolution such that the radiation administered to the patient is relatively lower than in a conventional CT scan. The system 100 analyzes the image data or image generated from the preliminary scan data at step 408 to identify target ROI 410, such as a region indicative of an anomaly such as a lung nodule or lesion.

Figure 5:
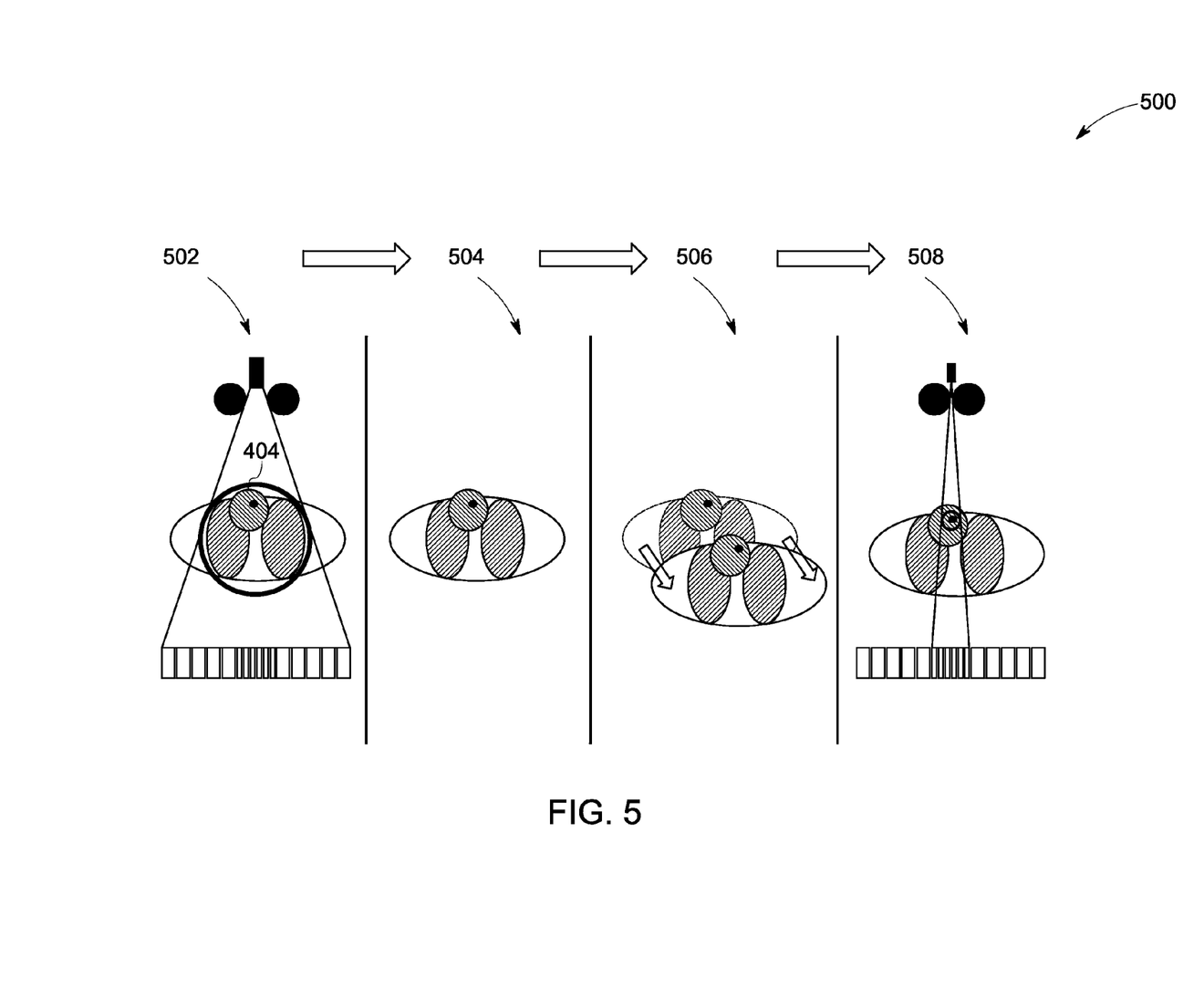
FIG. 5 is a flowchart depicting an exemplary sequence of operations for imaging cardiac tissues of the subject using the method described with reference to FIG. 3, in accordance with aspects of the present technique.

Based on the identified ROI, at 412, the subject 202 is shifted or moved axially to align the target ROI at the center of rotation of the system 100. Further, the system 100 collimates the X-ray beams 106 so as to focus specifically over the target ROI. Alternatively, the system 100 employs a high-resolution portion 414 of the detector array 108 to image the target ROI at 416. The system 100 then uses the targeted scan data to reconstruct one or more images of the target ROI. In certain implementations, the system 100 uses the preliminary scan data in addition to the targeted scan data for reconstructing one or more high-resolution images of the target ROI, for example, using interior tomography or using the preliminary scan sinogram data and/or image. Further, FIG. 5 depicts an exemplary sequence 500 of operations 502-508, similar to the operations illustrated in FIG. 4, for identifying and imaging anomalies such as a stenosis or plaque in the cardiac tissues 404 using the method described with reference to FIG. 3.

Figure 6:
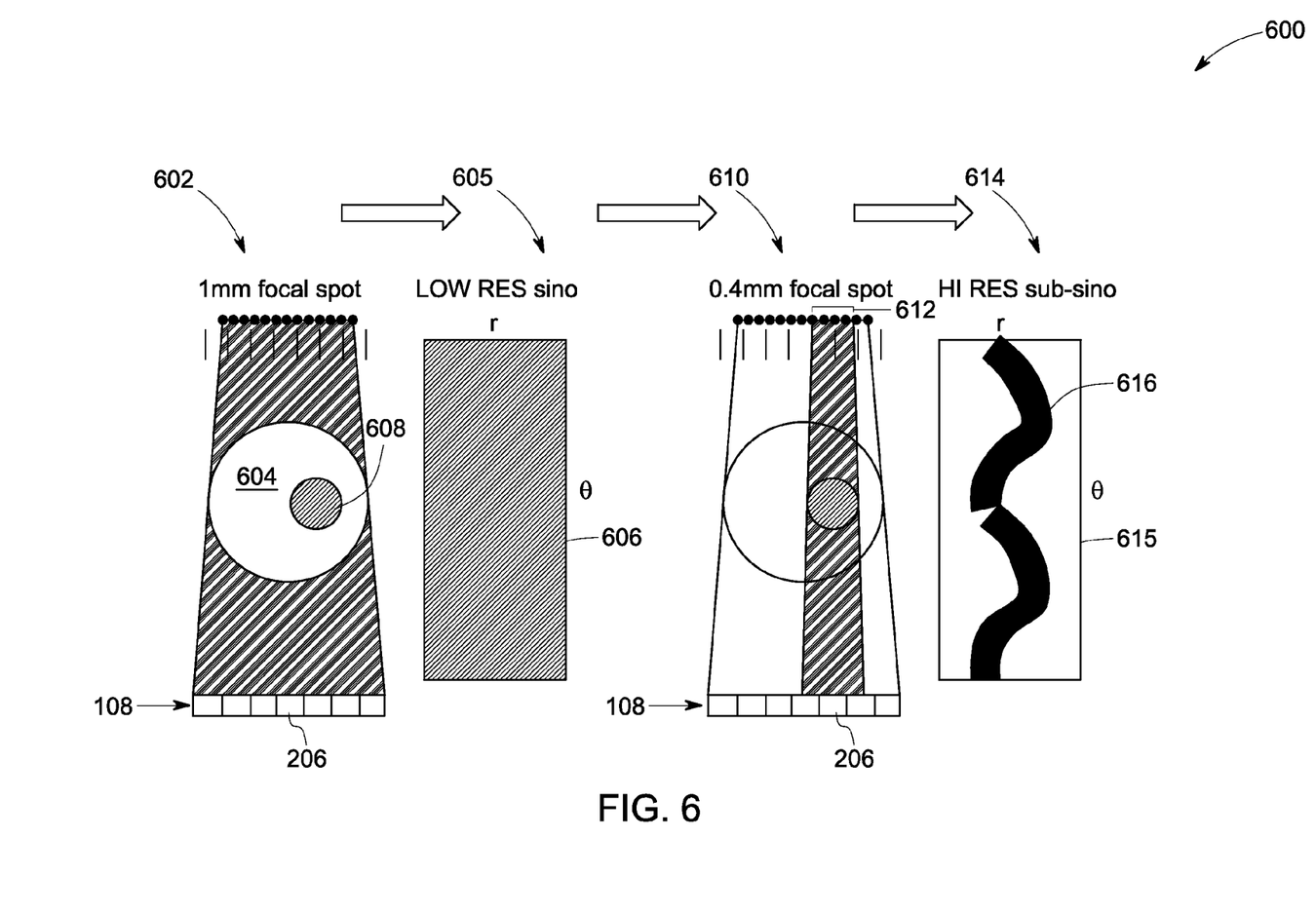
FIG. 6 illustrates an exemplary configuration for image data acquisition using multiple radiation sources, in accordance with aspects of the present technique.

FIGS. 6-9 illustrate certain exemplary configurations for image data acquisition using the method of FIG. 3. FIG. 6, for example, illustrates a graphical representation 600 corresponding to data acquisition using a detector array including high-resolution detector elements. In FIG. 6, element 602 corresponds to an exemplary configuration for the preliminary scan. In the embodiment illustrated in FIG. 6, the entire detector array 108 includes high-resolution photon counting detector elements 206 having a size of about 0.3 millimeter (mm). As indicated by the element 602, the preliminary scan of a first FOV 604 is performed using a 1 mm focal spot and the entire detector array 108. Additionally, at 605, a corresponding sinogram 606 depicting the values measured from the X-ray beams 106 during the preliminary scan is generated to identify a target ROI 608.

The target ROI 608 is then imaged using a targeted scan at 610 by reducing the focal spot size to about 0.4 mm. In particular, the focal spot size is reduced by selectively activating specific spots 612 on the radiation source corresponding to the approximate position of the target ROI at 614 as a function of gantry rotation angle. Such targeted scanning of the target ROI is used to generate a high-resolution sinogram 615, where 'θ' corresponds to the angle of the X-ray beams 106 used for acquiring the target image data, whereas 'r' corresponds to a radial distance of the X-ray beams 106 to the center of rotation. In particular, the sinogram 615 illustrates the data 616 acquired using the subset of the X-ray beams 106 employed to illuminate the target ROI.

Figure 7:
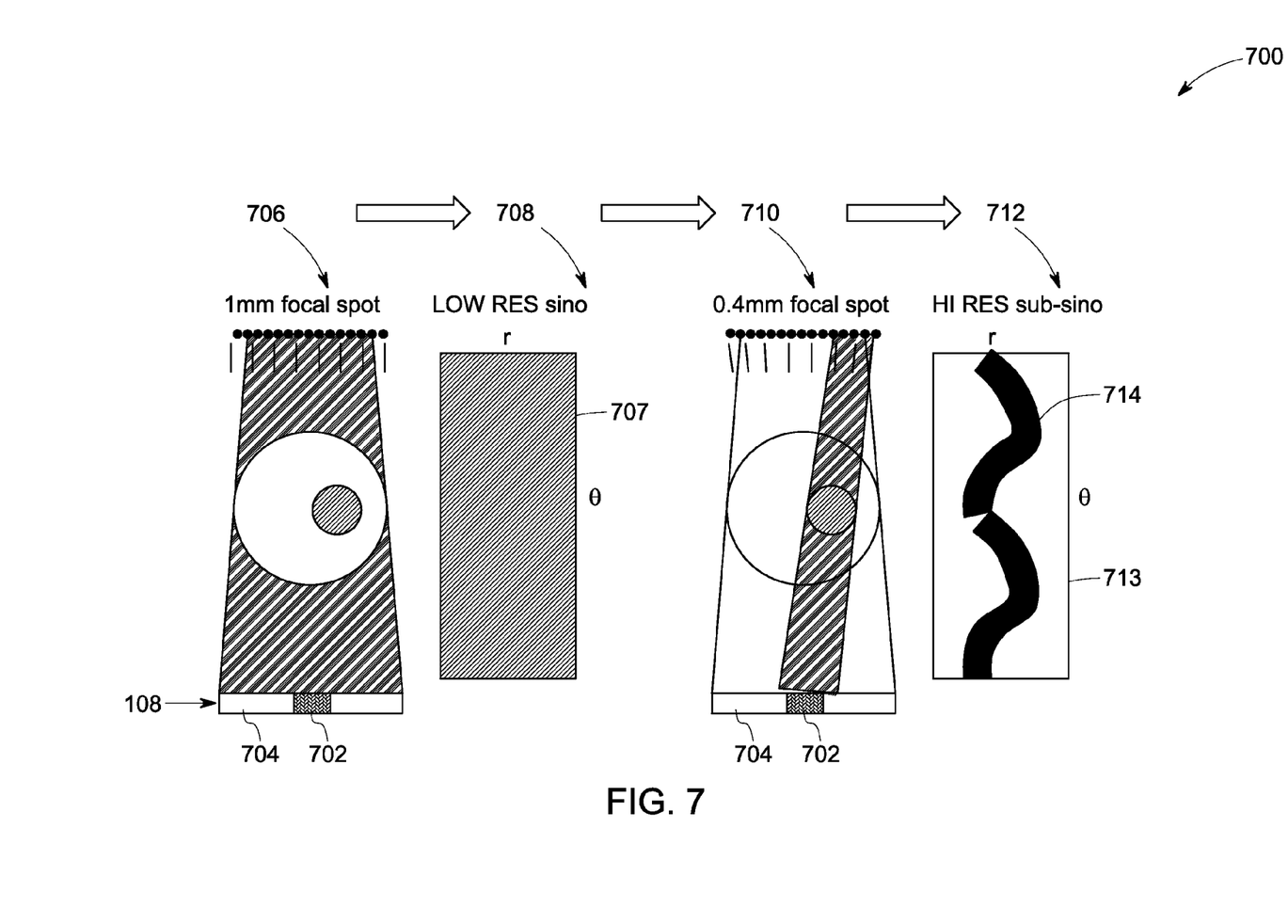
FIG. 7 illustrates another exemplary configuration for image data acquisition using distributed radiation sources and a hybrid detector array, in accordance with aspects of the present technique.

Further, FIG. 7 illustrates a graphical representation 700 corresponding to data acquisition using the hybrid detector array 108 and a plurality of distributed radiation sources. In the configuration illustrated in FIG. 7, the detector array 108 includes at least one high-resolution portion 702, for example, the central portion including high-resolution PC detector elements and one or more lower-resolution portions 704 of EI detector elements. At 706, the preliminary scan is performed to scan the first FOV to generate a corresponding sinogram 707 at 708.

Additionally, the system uses the collimators to direct X-ray beams towards the central high-resolution portion of the detector array 108. Alternatively, the system uses the collimators to direct the X-ray beam, for example, towards the left or right of a previous configuration to select, for example, a 0.4 mm focal spot in the center for directing the X-ray beams over the target ROI. Collimation of the X-ray beams, in on example, may be achieved by activating individual elements of the distributed source as a function of gantry angle corresponding to the location of the target ROI. It may be noted that in certain embodiments, collimation obviates the step of positioning the patient to realign the target ROI for the high-resolution second scan at 710. Further, at 712, the system generates a sinogram 713 illustrating the data 714 acquired using the subset of the X-ray beams 106 employed to illuminate the target ROI.

Figure 8:
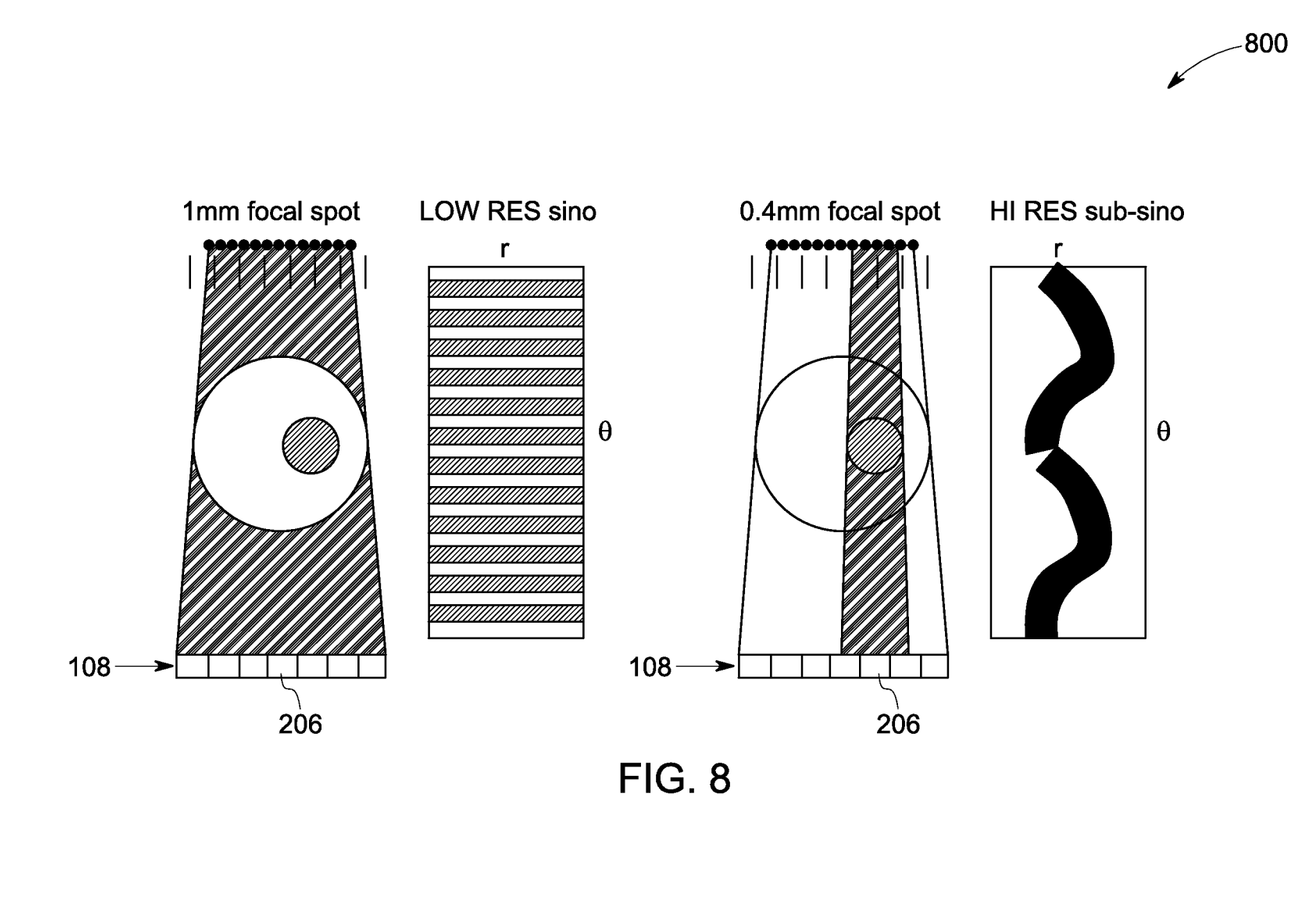
FIG. 8 illustrates an exemplary configuration for image data acquisition using multiple radiation sources and a subset of view angles, in accordance with aspects of the present technique.
Figure 9:
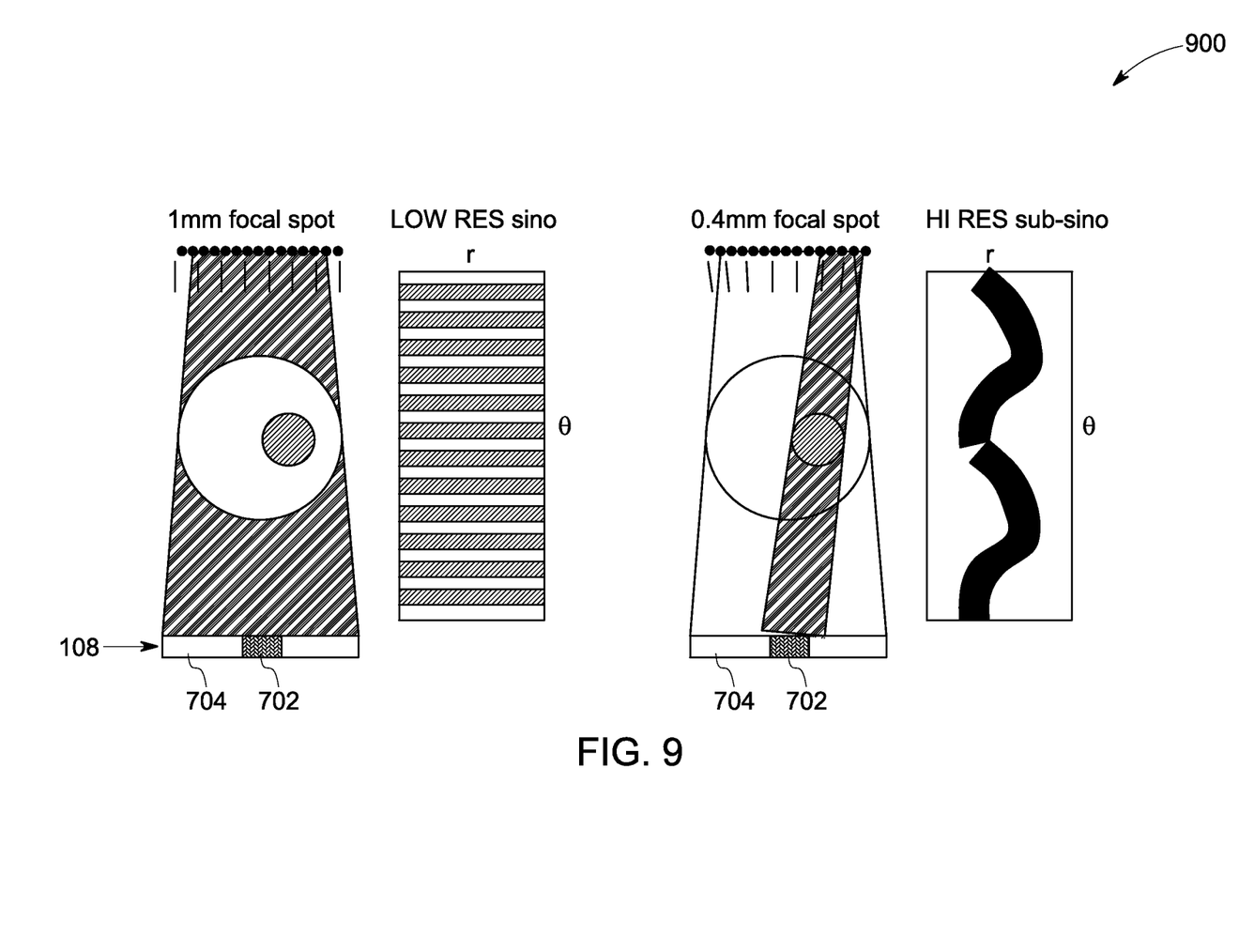
FIG. 9 illustrates another exemplary configuration for image data acquisition using a hybrid detector, multiple radiation sources and a subset of view angles, in accordance with aspects of the present technique.

Further, FIGS. 8 and 9 illustrate exemplary diagrams 800 and 900 illustrating the data acquisition, similar to the data acquisition described with reference to FIG. 6 and FIG. 7, respectively, but using only a subset of view angles used in FIGS. 6 and 7. In certain embodiments, the specific subset of the views scanned is based on one or more of the position of the target ROI, the size of the target ROI, the desired spatial resolution, the desired image noise level and the desired dose level.

The present systems and methods, thus, disclose an efficient technique for acquiring image data for facilitating reconstruction of an image of a specific region of a subject in high spatial resolution. Employing the high-resolution scan only for the target ROI reduces the radiation dose typically administered to the patient. Further, reconfiguring one or more parameters of the system components for changing the position and resolution for different scans enables use of a cost-effective imaging system. Additionally, use of preliminary image data along with the target image data allows for reconstructing features of interest in high spatial resolution for accurate and early diagnosis of conditions such as cardiac vulnerable plaque, stenosis, lung lesions, nodules and chronic obstructive pulmonary disease. The present methods and system, thus, not only reduce radiation dose and refine image quality, but also increase system functionalities, and boost scanner throughput in biomedical and other imaging applications.

Furthermore, the foregoing examples, demonstrations, and process steps such as those that may be performed by the computing device 216 and the control mechanism 208 may be implemented by suitable code on a processor-based system, such as a general-purpose or special-purpose computer. It should also be noted that different implementations of the present technique may perform some or all of the steps described herein in different orders or substantially concurrently, that is, in parallel. In addition, the functions may be implemented in a variety of programming languages, including but not limited to Python, C++ or Java. Such code may be stored or adapted for storage on one or more tangible, machine-readable media, such as on data repository chips, local or remote hard disks, optical disks (that is, CDs or DVDs), solid-state drives or other media, which may be accessed by the processor-based system to execute the stored code.

Although specific features of various embodiments of the invention may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and techniques.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for imaging a subject, comprising:
  acquiring preliminary image data corresponding to a first field of view of the subject at a first resolution using an imaging system comprising one or more radiation sources and a single hybrid detector responsive to radiation received from the one or more radiation sources, wherein the preliminary image data is acquired using at least one section of the hybrid detector comprising one or more detector elements having the first resolution and a first size, wherein the hybrid detector further comprises at least another section comprising one or more detector elements having a second resolution and a second size such that the detector elements having the second size are smaller than the detector elements having the first size;
  identifying a target region of interest based on the preliminary image data;
  positioning the subject so as to align the target region of interest along a designated axis;
  configuring one or more parameters associated with the radiation sources, the hybrid detector, a gantry associated with the imaging system, or combinations thereof, wherein configuring the one or more parameters comprises:
    operating in a multi-energy mode for the second resolution, wherein the multi-energy mode comprises switching tube voltage of the one or more radiation sources between one or more voltages;
    selectively focusing on the section of the hybrid detector comprising one or more detector elements having the second resolution and the second size for acquiring target image data corresponding to the target region of interest at the second resolution using a target focal spot size, wherein the target focal spot size is smaller than a preliminary focal spot size used for acquiring the preliminary image data at the first resolution;
    selectively switching the detector elements having the first size to a low resolution operating mode via a switching interface for acquiring the preliminary image data at the first resolution and selectively switching the detector elements having the second size to a high resolution operating mode via the switching interface for acquiring the target image data at the second resolution, wherein the second resolution is greater than the first resolution; and
  reconstructing one or more images corresponding to at least the target region of interest using the target image data, the preliminary image data, or a combination thereof, wherein the combination of operating in the multi-energy mode, selectively focusing on the target focal spot size, and selectively switching to the high resolution operating mode is configured to reduce dosage administered to the subject.

2. The method of claim 1, wherein the preliminary image data is acquired using the entire hybrid detector.

3. The method of claim 1, wherein configuring one or more parameters comprises collimating the one or more radiation sources to focus on the section of the hybrid detector having the second resolution for acquiring the target image data.

4. The method of claim 1, further comprising determining the first resolution by summing signal received from a plurality of detector elements in the hybrid detector and determining the second resolution by having each of the plurality of detector elements of the hybrid detector read out individually.

5. The method of claim 1, wherein the one or more radiation sources comprise distributed radiation sources, and wherein at least one of the distributed radiation sources is configured to focus on the section of the hybrid detector having the first resolution for acquiring the preliminary image data, and at least another of the distributed radiation sources is configured to focus on the section of the hybrid detector having the second resolution for acquiring the target image data.

6. The method of claim 1, wherein the multi-energy mode further comprises switching the hybrid detector between at least one of an energy-integrating mode and a photon counting mode for acquiring the preliminary image data at the first resolution and acquiring the target image data at the second resolution, respectively.

7. The method of claim 1, further comprising analyzing the one or more images corresponding to at least the target region of interest for determining one or more of an anatomical structure, size, thickness, eccentricity, density, mass, composition and nature of a nodule, a lesion, a stenosis, plaque, or combinations thereof, of biological tissues corresponding to the target region of interest.

8. The method of claim 1, further comprising analyzing one or more of the preliminary image data and the target image data to determine if the imaging system is centered on a desired region of interest of the subject.

9. The method of claim 1, wherein identifying the target region of interest comprises detecting a structural anomaly by evaluating the preliminary image data, using operator input, automated tools, computer aided analysis, prior examination data, or combinations thereof.

10. The method of claim 1, wherein positioning the subject comprises centering the target region along a longitudinal axis of rotation of the gantry.

11. The method of claim 1, wherein positioning the subject comprises centering the target region at iso-center in a transaxial plane.

12. The method of claim 1, wherein reconstructing one or more images comprises using interior tomographic reconstruction using truncated projection data to generate one or more images corresponding to the target region of interest.

13. The method of claim 1, wherein reconstructing one or more images comprises using sinogram data generated from the preliminary image data to supplement sinogram data generated from the targeted scan for use in reconstructing the one or more images corresponding to the target region of interest.

14. A method for imaging a subject, comprising:
acquiring preliminary image data corresponding to a first field of view of the subject at a first resolution using an imaging system comprising one or more radiation sources and at least one hybrid detector responsive to radiation received from the one or more radiation sources, wherein the preliminary image data is acquired by selectively switching a desired set of detector elements in at least one section of the hybrid detector having the first resolution and a first size to a low resolution operating mode via a switching interface;
automatically identifying a target region of interest based on the preliminary image data;
configuring one or more parameters associated with the radiation sources, the hybrid detector, a gantry associated with the imaging system, or combinations thereof, wherein configuring the one or more parameters comprises:
operating in a multi-energy mode for the second resolution, wherein the multi-energy mode comprises switching tube voltage of the one or more radiation sources between one or more voltages;
selectively focusing on another section of the hybrid detector comprising one or more detector elements having the second resolution and the second size for acquiring target image data corresponding to the target region of interest at the second resolution using a target focal spot size, wherein the target focal spot size is smaller than a preliminary focal spot size used for acquiring the preliminary image data at the first resolution;
selectively switching the detector elements having the second resolution and the second size in the hybrid detector to a high resolution operating mode via the switching interface for tracking the target region of interest and acquiring target image data corresponding to the target region of interest at the second resolution, wherein the second resolution is greater than the first resolution; and
reconstructing one or more images corresponding to at least the target region of interest using the target image data, the preliminary image data, or a combination thereof.

15. The method of claim 14, wherein tracking the target region of interest comprises configuring the focusing parameters of the one or more radiation sources to focus on the target region of interest, collimating the one or more radiation sources to focus the radiation on the target region of interest, selectively activating the section of the hybrid detector having the second resolution, or combinations thereof.

16. An imaging system, comprising:
one or more radiation sources that emit radiation towards a subject;
a single hybrid detector that receives the radiation from the one or more radiation sources, wherein the hybrid detector comprises at least one section comprising one or more detector elements having a first resolution and a first size, and at least another section comprising one or more detector elements having a second resolution and a second size such that the detector elements having the second size are smaller than the detector elements having the first size;
a switching interface that selectively switches the detector elements having the first size, the second size, or a combination thereof, between a low resolution operating mode and a high resolution operating mode; and
a computing device coupled to one or more of the radiation sources, the hybrid detector, the switching interface, and the data acquisition unit, wherein the computing device:
directs a data acquisition system coupled to the imaging system to acquire preliminary image data corresponding to a first field of view of the subject at a first resolution using the section of the hybrid detector having the first resolution;
identifies a target region of interest based on the preliminary image data;
positions the subject for aligning the target region of interest along a designated axis;
configures one or more parameters associated with the one or more radiation sources, the one or more detectors, a gantry associated with the imaging system, or combinations thereof by:
operating in a multi-energy mode for the second resolution, wherein the multi-energy mode comprises switching tube voltage of the one or more radiation sources between one or more voltages;
selectively focusing on the section of the hybrid detector comprising the one or more detector elements having the second resolution and the second size for acquiring the target image data using a target focal spot size, wherein the target focal spot size is smaller than a preliminary focal spot size used for acquiring the preliminary image data at the first resolution;
selectively switching the detector elements having the first size to the low resolution operating mode via the switching interface for acquiring the preliminary image data at the first resolution and selectively switching the detector elements having the second size to the high resolution operating mode via the switching interface for acquiring target image data corresponding to the target region of interest at the second resolution, wherein the second resolution is greater than the first resolution; and
reconstructs one or more images corresponding to at least the target region of interest using the target image data, the preliminary image data, or a combination thereof.

17. The imaging system of claim 16, wherein the imaging system comprises a computed tomography system.

18. A non-transitory computer readable medium that stores instructions executable by one or more processors to perform a method for imaging a subject, comprising:
acquiring preliminary image data corresponding to a first field of view of the subject at a first resolution using an imaging system comprising one or more radiation sources and at least one hybrid detector responsive to radiation received from the one or more radiation sources, wherein the preliminary image data is acquired by selectively switching a desired set of detector elements in at least one section of the hybrid detector having the first resolution and a first size to a low resolution operating mode via a switching interface;
automatically identifying a target region of interest based on the preliminary image data;

configuring one or more parameters associated with the radiation sources, the hybrid detector, a gantry associated with the imaging system, or combinations thereof, wherein configuring the one or more parameters comprises:
  operating in a multi-energy mode for the second resolution, wherein the multi-energy mode comprises switching tube voltage of the one or more radiation sources between one or more voltages;
  selectively focusing on another section of the hybrid detector comprising one or more detector elements having the second resolution and the second size for acquiring target image data corresponding to the target region of interest at the second resolution using a target focal spot size, wherein the target focal spot size is smaller than a preliminary focal spot size used for acquiring the preliminary image data at the first resolution;
  selectively switching the detector elements having the second resolution and the second size in the hybrid detector to a high resolution operating mode via the switching interface for tracking the target region of interest and acquiring target image data corresponding to the target region of interest at the second resolution, wherein the second resolution is greater than the first resolution; and
reconstructing one or more images corresponding to at least the target region of interest using the target image data, the preliminary image data, or a combination thereof.

* * * * *